US010625249B2

(12) United States Patent
Driess et al.

(10) Patent No.: US 10,625,249 B2
(45) Date of Patent: Apr. 21, 2020

(54) CATALYST FOR THE HYDROFORMYLATION OF OLEFINS, AND USE THEREOF

(71) Applicant: TECHNISCHE UNIVERSITAET BERLIN, Berlin (DE)

(72) Inventors: Matthias Driess, Berlin (DE);
Reinhard Schomaecker, Berlin (DE);
Burgert Blom, SV Maastricht (NL);
Marcel Schmidt, Berlin (DE)

(73) Assignee: TECHNISCHE UNIVERSITÄT BERLIN, Berlin (DE)

( * ) Notice: Subject to any disclaimer, the term of this patent is extended or adjusted under 35 U.S.C. 154(b) by 0 days.

(21) Appl. No.: 16/093,764

(22) PCT Filed: Apr. 12, 2017

(86) PCT No.: PCT/EP2017/058800
§ 371 (c)(1),
(2) Date: Oct. 15, 2018

(87) PCT Pub. No.: WO2017/178536
PCT Pub. Date: Oct. 19, 2017

(65) Prior Publication Data
US 2019/0126259 A1    May 2, 2019

(30) Foreign Application Priority Data
Apr. 14, 2016  (DE) .......................... 10 2016 206 303

(51) Int. Cl.
    *B01J 31/00*      (2006.01)
    *C07C 45/50*      (2006.01)
    *B01J 31/16*      (2006.01)
    *C07F 7/10*       (2006.01)
    *C07F 17/02*      (2006.01)
    *B01J 31/22*      (2006.01)
    *B01J 31/24*      (2006.01)

(52) U.S. Cl.
    CPC ....... *B01J 31/1608* (2013.01); *B01J 31/2295* (2013.01); *B01J 31/24* (2013.01); *C07C 45/50* (2013.01); *C07F 7/10* (2013.01); *C07F 17/02* (2013.01); *B01J 2231/321* (2013.01); *B01J 2531/842* (2013.01)

(58) Field of Classification Search
    CPC ........ B01J 31/1608; B01J 31/24; C07C 45/50
    See application file for complete search history.

(56) References Cited
U.S. PATENT DOCUMENTS 6,103,867 A    8/2000  Slany et al.
6,346,324 B1   2/2002  Queisser et al.
6,541,564 B2   4/2003  Schmid et al.
6,852,662 B2   2/2005  Queisser et al.
2009/0299099 A1  12/2009  Tolleson et al.
2011/0160412 A1   6/2011  Thieuleux et al.

FOREIGN PATENT DOCUMENTS

WO    200033956 A1   6/2000

OTHER PUBLICATIONS

Wang et al. An Isolable Bis-Silylene Oxide ("Disilylenoxane") and Its Metal Coordination. Journal of the American Chemical Society, 132, 15890-15892. (Year: 2010).*
Azhakar et al. The group 7 metal carbonyl complexes from a stable heteroleptic silylene PhC(NtBu)2 SiNPh2. Dalton Transactions, 41, 12096-12100. (Year: 2012).*
Beller, M et al. Progress in hydroformylation carbonylation. J. Mol. Catal. A Chem. 104 (1995) 17-85.
Blom, B. et al. From Unsymmetrically Substituted Benzamidinato and Guanidinato Dichlorohydridosilanes to Novel Hydrido N-Heterocyclic Silylene Iron Complexes Organometallics 2014, 33 5272-5282.
Blom, B. et al. Highly Electron-Rich Pincer-Type Iron Complexes Bearing Innocent Bis(metallylene)pyridine Ligands: Syntheses, Structures, and Catalytic Activity Organometallics 2014, 33, 6885-6897.
Blom, B. et al. New Vistas in N-Heterocyclic Silylene (NHSi) Transition-Metal Coordination Chemistry: Syntheses, Structures and Reactivity towards Activation of Small Molecules. Chem.—A Eur. J. 19 (2013) 40-62.
Blom, B. et al. N-heterocyclic silylene complexes in catalysis: new frontiers in an emerging field. Inorg. Chem. Front. 1 (2014) 134.
Bortenschlager, M. et al. Rhodium-NHC-complexes as potent catalysts in the hydroformylation of 1-octene. J. Organomet. Chem. 690 (2005) 6233-6237.
Carlock, J.T. A Comparative Study of Triphenylamine, Tryphenylphospine, Triphenylarsine, Triphenylantimony and Triphenylbismuth as Ligands in the Rhodium-catalyzed Hydroformylation of 1-Dodecene. Tetrahedron 40 (1984) 185-187.
Chen, A.C. et al. Rhodium Carbene Complexes: Highly Selective Catalysts for the Hydroformylation of Styrene Derivatives. Organometallics 19 (2000) 3459-3461.

(Continued)

Primary Examiner — Sikarl A Witherspoon
(74) Attorney, Agent, or Firm — Brooks Kushman P.C.

(57) ABSTRACT

A catalyst for the hydroformylation of at least one olefin, having a ligand fo the general formula (1) —$R^1$, $R^2$, $R^3$ selected from the group including substituted and non-substituted alkyl, substituted and non-substituted aryl, substituted and non-substituted alkenyl, substituted and non-substituted alkinyl, substituted and non-substituted cycloalkyl, and substituted and non-substituted heterocycles, wherein $R^1$, $R^2$ and $R^3$ can each be the same or different, L is selected from a group having a sandwich complex, an oxygen group, substituted and non-substituted alkylene or heterocycles, and substituted aryl or heteroaryl; and aryl and heteroaryl is each substituted with groups which contain at least two heteroatoms and are coupled to the Si via the at least two heteroatoms of the substituents, —n=1-10, preferably 1-5, particularly preferably 1, 2, or 3; and the ligand is coupled to the metal M from the group VIIIb of the periodic table of elements via the Si group.

10 Claims, 1 Drawing Sheet

(56) References Cited

OTHER PUBLICATIONS

Cornils, B. et al. Otto Roelen, Pioneer in Industrial Homogeneous Catalysis Angew. Chem. Int. Ed. 33 (1994) 2144-2163.

Cornils, B. et al. Introducing TPPTS and related ligands for industrial biphasic processes. J. Organomet. Chem. 502 (1995) 177-186.

Damoense, L. Recent advances in high-pressure infrared and NMR techniques for the determination of catalytically active species in rhodium- and cobalt-catalysed hydroformylation reactions. Coord. Chem. Rev. 248 (2004) 2393-2407.

Del Rio, I. et al. Mechanistic study of the hydroformylation of styrene catalyzed by the rhodium:BDPP system. J. Organomet. Chem. 608 (2000) 115-121.

Denk, M. et al. Synthesis and Structure of a Stable Silylene. J. Am. Chem. Soc. 116 (1994) 2691-2692.

Franke, R. et al. Applied Hydroformylation Chem. Rev. 112 (2012) 5675-5732.

Gil, W. and Trzeciak A.M. N-Heterocyclic carbene-rhodium complexes as catalysts for hydroformylation and related reactions. Coord. Chem. Rev. 255 (2011) 473-483.

Haaf, M. et al. Stable Silylenes. Acc. Chem. Res. 33 (2000) 704-714.

Hill, N.J. and West, R. Recent developments in the chemistry of stable silylenes J. Organomet. Chem. 689 (2004) 4165-4183.

Jacobs, I. et al. Comparison of the Full Catalytic Cycle of Hydroformylation Mediated by Mono- and Bis-Ligated Triphenylphosphine-Rhodium Complexes by Using DFT Calculations. ChemCatChem 7 (2015) 1708-1718.

Kranenburg, M. et al. New Diphosphine Ligands Based on Heterocyclic Aromatics Inducing Very High Regioselectivity in Rhodium-Catalyzed Hydroformylation: Effect of the Bite Angle. Organometallics 14 (1995) 3081-3089.

Pruett, R.L. and a Low-Pressure System for Producing Normal Aldehydes by Hydroformylation of a Olefins. J. Org. Chem. 34 (1969) 327-330.

Schmedake, T. et al. Electronic and steric properties of stable silylene ligands in metal(0) carbonyl complexes. Organomet. Chem. 636 (2001) 17-25.

So, C.-W. et al. Synthesis and Structures of Heteroleptic Silylenes. J. Am. Chem. Soc. 129 (2007) 12049-54.

Srivastava, V.K. et al. The Rh, Co, Ru metal-catalyzed hydroformylation of hex-1-ene using triphenylphosphine, triphenylarsine and triphenylantimony as ligands. Appl. Catal. A Gen. 282 (2005) 31-38.

Tolman, C.A. Steric Effects of Phosphorus Ligands in Organometallic Chemistry and Homogeneous Catalysis. Chem. Rev. 77 (1976) 313-348.

Van Rooy, A. et al. Rhodium-catalysed hydroformylation of branched 1-alkenes; bulky phosphite vs. triphenylphosphine as modifying ligand. J. Organomet. Chem. 507 (1996) 69-73.

Wang, W. Bis(silylenyl)- and Bis(germylenyl)-Angew. Chemie 124 Substituted Ferrocenes: Synthesis, Structure, and Catalytic Applications of Bidentate Silicon(II)—Cobalt Complexes. (2012) 6271-6275.

International Search Report for PCT/EP2017/058800 with English Translation, issued by the European Patent Office dated Oct. 16, 2018. All together 14 pages.

Hendriksen, D. et al Selective rhodium-catalyzed hydroformylation with the tri- and tetraphosphine ligands (CH3) 1,0Si(CH2CH2PPh2)3,4. Formation of Rh[Si(CH2CH2PPh2)3](CO) via CH3—Si bond cleavage and structure of this Rh(I)—Si bonded complex, Organometallics, Jan. 1, 1989 (Jan. 1, 1989), p. 1153.

* cited by examiner

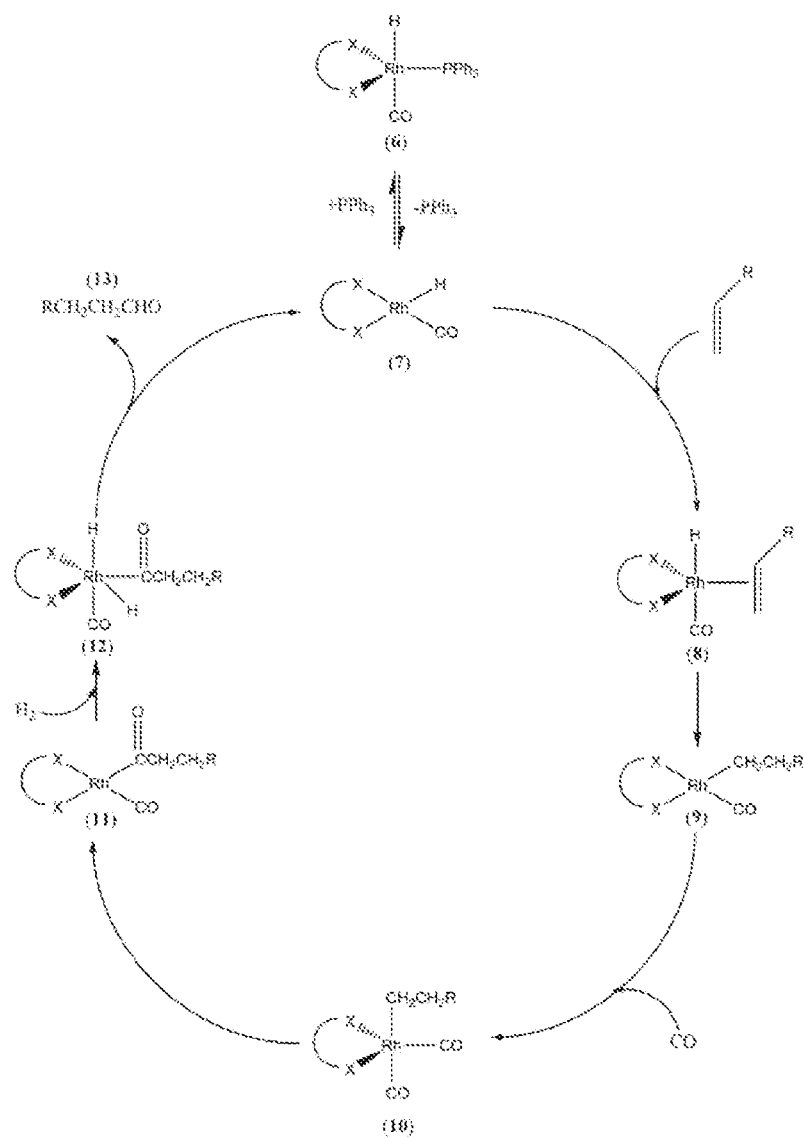

CATALYST FOR THE HYDROFORMYLATION OF OLEFINS, AND USE THEREOF

CROSS REFERENCE TO RELATED APPLICATIONS

This application is U.S. National Phase of PCT Application Number PCT/EP2017/058800, filed on Apr. 12, 2017, which claims priority to German Patent Application Number 10 2016 206 303.0, filed on Apr. 14, 2016, the disclosures of which are is incorporated in their entirety by reference herein.

BACKGROUND

The present invention relates to a catalyst for the hydroformylation of at least one olefin, a method for using of such a catalyst and a method for the hydroformylation of olefins.

Hydroformylation is an important industrial process in which an olefin or alkene is converted with carbon monoxide and hydrogen (synthesis gas) to an aldehyde. The total volume of aldehydes produced by hydroformylation currently averages over 10 million tons per year.

For the majority of the alkenes, several products can be formed depending on the regioselectivity of the addition reaction. The linear and branched product are generally obtained as a mixture, wherein the linear product is preferred for industrial applications. The primarily occurring aldehydes are usually hydrogenated to alcohols, which are used as plasticizers for PVC or as solvents, or are further processed into polymers.

There are currently two main methods for the hydroformylation of alkenes. One method involves the use of a cobalt catalyst, which in general is used for the production of higher aldehydes and alcohols with a chain length of C>5. As separation of the homogenous catalyst is difficult in the case of medium- or long-chain olefins, cobalt catalysts, which are cheaper compared to rhodium, are used in this case.

In contrast, ligand-modified rhodium catalysts are used for short-chain olefins, as in this case the catalyst complex can be quantitatively separated (e.g. the Ruhrchemie/Rhône-Poulenc method). Rhodium-catalyzed hydroformylation reactions are carried out under relatively mild conditions and are generally used for the hydroformylation of ethene and propene, but also for the conversion of 2-propen-1-ol to butane diol.

There is a need for more selective and active catalysts for the formation of aldehydes that can also be used for higher aldehydes. Ligands used in catalyst complexes are of special importance for increasing the activity and selectivity of hydroformylation.

The selection of a suitable ligand is of decisive importance for the activity and selectivity of hydroformylation. Accordingly, research is focused on the synthesis and coordination chemistry of new ligands. It is advantageous that the number of different ligands for use in hydroformylation is virtually infinite. Up to now, phosphorus, nitrogen, or carbene ligands have chiefly been used for hydroformylation, in particular for rhodium-catalyzed hydroformylation. Phosphines, with three alkyl groups bonded to the phosphorus atom, and phosphites, with three alkoxy groups bonded to the phosphorus atom, are of considerable interest, wherein catalysts modified with phosphites often show stronger activity. The steric properties of the ligands are also a critical parameter with respect to the regioselectivity of hydroformylation.

Because of the major economic significance of hydroformylation, however, there is still a need for catalysts that show both improved activity and improved regioselectivity.

SUMMARY

Accordingly, the object of the present invention is to develop novel catalyst systems for the hydroformylation of olefins.

This object is achieved by means of a catalyst having features as described herein.

Accordingly, a catalyst for the hydroformylation of at least one olefin is provided that comprises a ligand of general formula (I)

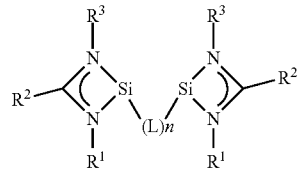

wherein $R^1$, $R^2$, and $R^3$ are selected from the group comprising substituted and unsubstituted alkyl, substituted and unsubstituted aryl, substituted and unsubstituted alkenyl, substituted and unsubstituted alkinyl, substituted and unsubstituted cycloalkyl, substituted and unsubstituted heterocycles, wherein $R^1$, $R^2$ and $R^3$ can each be the same or different, L is selected from a group comprising a sandwich complex, an oxygen group, substituted and unsubstituted alkylene or heteroalkylene, substituted aryl or heteroaryl, wherein aryl and heteroaryl are each substituted with groups comprising at least two heteroatoms and are coupled to the Si via the at least two heteroatoms of the substituents, n=1-10, preferably 1-5, particularly preferably 1, 2, or 3; and wherein the ligand is coupled to the metal M from group VIIIb of the periodic table of elements via the Si group.

A catalyst for the hydroformylation of olefins is thus provided that comprises N-heterocyclic silylene (NHSi) ligands. The N-heterocyclic silylenes used here as ligands are heavy analogs of the N-heterocyclic carbenes (NHCs) that possess a free electron pair on the silicon, allowing them to function as ligands for metal-catalyzed reactions. The particular characteristic of the N-heterocyclic silylenes is that they act both as a strong σ donor and a π acceptor, which allows the electronic properties of the metal center of the catalyst to be decisively modified.

The N-heterocyclic silylenes used as ligands are bidentate ligands. Because of their bidentate properties, only one equivalent of the ligand binds to the metal center, thus leaving a free coordination site for binding of the olefin substrate to the catalytic center.

In an embodiment, cobalt or rhodium is used as a metal M, wherein rhodium is of particular significance for catalyzed homogeneous hydroformylation.

In a variant of the present catalyst, the linker L is in the form of a metallocene complex, i.e. a metallocene complex of two respectively substituted or unsubstituted cyclopentadiene anions bound to a metal center. Typical metallocenes are ferrocene, titanocene dichloride, and vanadocene dichloride, wherein ferrocene is particularly preferred as the linker L.

In another variant of the present catalyst, the linker L is present in the form of a phenyl or pyridine ring, each of which is substituted with at least two groups comprising a heteroatom (for coupling to the Si). In this case, oxygen and nitrogen are preferred as heteroatoms. The phenyl and pyridine ring can also have further substituents.

In the case of a phenyl ring as the linker L, said phenyl ring can have at least two substituents, each of which comprises an oxygen atom. Here, the oxygen atom can be directly bonded to the phenyl ring (—O-phenyl-O—) or can be incorporated into an alkyl radical that is bonded to the phenyl ring (e.g. —O—$CH_2$-phenyl-$CH_2$—O—).

In the case of a pyridine ring as the linker L, said pyridine ring can have at least two substituents, each of which comprises a nitrogen atom. Here, the nitrogen atom can be directly bonded to the pyridine ring (e.g. (—NH-pyridine-NH—) or can be incorporated into an alkyl radical that is bonded to the pyridine ring (e.g. —NH—$CH_2$-pyridine-$CH_2$—NH—). In a particularly preferred variant, a pyridine ring according to —$NR_x$-pyridine-$NR_x$— is used as the linker L, wherein $R_x$ is a $C_1$-$C_5$ alkyl, preferably a methyl, ethyl or propyl, in particular an ethyl.

The substituents $R^1$, $R^2$ and $R^3$ of the ligand are preferably selected from a group comprising substituted and unsubstituted $C_1$-$C_{12}$ alkyl, substituted and unsubstituted phenyl, substituted and unsubstituted $C_5$-$C_6$ heteroaryl, substituted and unsubstituted naphthyl, substituted and unsubstituted $C_3$-$C_{10}$ cycloalkyl, substituted and unsubstituted $C_7$-$C_{18}$ alkylphenyl, substituted and unsubstituted $C_5$-$C_7$ cycloalkenyl, substituted and unsubstituted $C_2$-$C_7$ heteroalkylene.

In a variant, the substituents $R^1$, $R^2$ and $R^3$ of the ligand are selected from a group comprising methyl, ethyl, n-propyl, isopropyl, n-butyl, s-butyl, t-butyl, pentyl, hexyl, cyclohexyl, vinyl, 1-propenyl, 2-propenyl, butenyl, or substituted and unsubstituted phenyl.

In this case, the radicals t-butyl, adamantane, and substituted and unsubstituted phenyl are particularly preferred. In the case of substituted phenyls, the substituents are preferably selected from a group comprising propyl or isopropyl.

In a particularly preferred variant embodiment, the NHSi ligand of the present catalyst has the following structure:

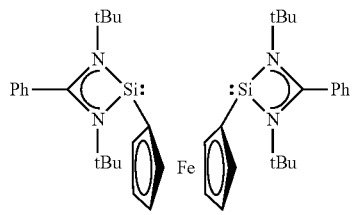

(1)

In a further preferred embodiment, the NHSi ligand of the present catalyst has one of the following structures:

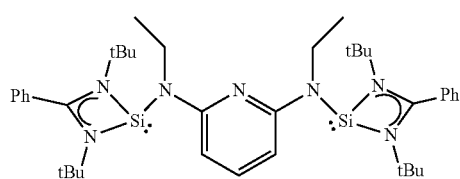

(2)

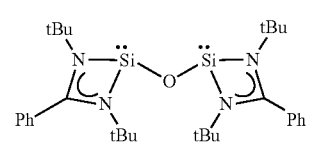

(3)

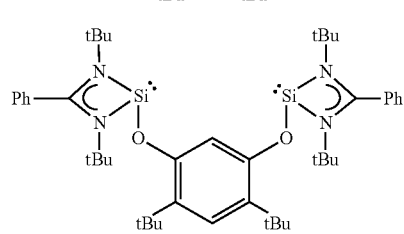

(4)

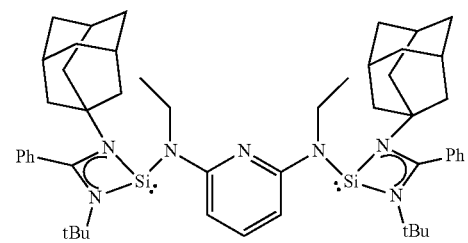

(5)

In the present context, in mixing of the ligand and metal under synthesis gas conditions, a complex in the form of a metal carbonyl hydride of general formula (II) is preferably formed:

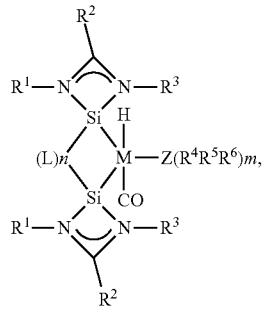

wherein

L, $R^1$, $R^2$, $R^3$ and M have the above meaning,

Z is a non-metallic element of group Va of the periodic table of elements or a CO ligand, $R^4$, $R^5$, and $R^6$ are selected from the group comprising substituted and unsubstituted alkyl, substituted and unsubstituted aryl, substituted and unsubstituted alkenyl, substituted and unsubstituted alkinyl, substituted and unsubstituted cycloalkyl, substituted and unsubstituted heterocycles, wherein $R^4$, $R^5$, and $R^6$ can each be the same or different, and m=0-3, preferably 3.

In the case of the complex of general structure (II), Z is in particular phosphorus or nitrogen, wherein phosphorus is particularly preferred.

The groups $R^4$, $R^5$, and $R^6$ are preferably selected from the group comprising substituted and unsubstituted $C_1$-$C_{12}$ alkyl, substituted and unsubstituted phenyl, substituted and unsubstituted $C_5$-$C_6$ heteroaryl, substituted and unsubstituted naphthyl, substituted and unsubstituted $C_3$-$C_7$ cycloalkyl, substituted and unsubstituted $C_7$-$C_{18}$ alkylphenyl, substituted and unsubstituted $C_5$-$C_7$ cycloalkenyl, and substituted and unsubstituted $C_2$-$C_7$ heteroalkylene.

In a particularly preferred variant, the groups $R^4$, $R^5$, and $R^6$ are selected from the group comprising substituted and unsubstituted phenyl.

In a variant, the present metal carbonyl hydride complex is obtained by reacting $HRh(CO)(PPh_3)_3$ analogously to the following reaction equation:

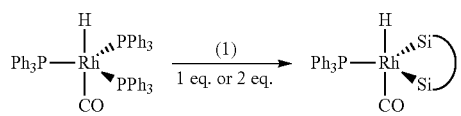

As can be seen from the above reaction equation, the phosphine ligands are substituted with the bidentate silylene ligands. As chelate ligands, the silylene ligands have a high complex formation constant and can easily substitute monodentate ligands. In the above complexing reaction, a phosphine ligand remains on the metal center, increasing the possibility of coordination of the olefin on the silylene-modified rhodium complex, as the phosphine ligand can be substituted with the olefin.

As mentioned above, each of the individual substituents $R^1$-$R^6$ can be in substituted or unsubstituted form.

The term "substituted" as used with "alkyl," "alkenyl," "aryl," etc., refers to the substitution of one or a plurality of atoms, as a rule H atoms, with one or a plurality of the following substituents, preferably with one or two of the following substituents: halogen, hydroxy, protected hydroxy, oxo, protected oxo, $C_3$-$C_7$ cycloalkyl, bicyclic alkyl, phenyl, naphthyl, amino, protected amino, monosubstituted amino, protected monosubstituted amino, disubstituted amino, guanidino, protected guanidino, a heterocyclic ring, a substituted heterocyclic ring, imidazolyl, indolyl, pyrrolidinyl, $C_1$-$C_{12}$ alkoxy, $C_1$-$C_{12}$ acyl, $C_1$-$C_{12}$ acyloxy, acryloyloxy, nitro, carboxy, protected carboxy, carbamoyl, cyano, methylsulfonylamino, thiol, $C_1$-$C_{10}$ alkylthio and $C_1$-$C_{10}$ alkylsulfonyl. The substituted alkyl groups, aryl groups, or alkenyl groups can be substituted once or several times, preferably once or twice, with the same or different substituents.

The term "$C_1$-$C_{12}$ alkyl" refers to radicals such as methyl, ethyl, n-propyl, isopropyl, n-butyl, isobutyl, s-butyl, t-butyl, amyl, t-amyl, hexyl, heptyl, octyl, nonyl, decyl, undecyl, dodecyl, and the like. Preferred $C_1$-$C_{12}$ alkyl groups are methyl, ethyl, isobutyl, s-butyl and isopropyl.

Examples of the above substituted alkyl groups include 2-oxo-prop-1-yl, 3-oxo-but-1-yl, cyanomethyl, nitromethyl, chloromethyl, hydroxymethyl, tetrahydropyranyloxymethyl, trityloxymethyl, propionyloxymethyl, aminomethyl, carboxymethyl, allyloxycarbonylmethyl, allyloxycarbonylaminomethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro (n-butyl), 2-aminopropyl, 1-chloroethyl, 2-chloroethyl, 1-bromoethyl, 2-bromomethyl, 1-fluoroethyl, 2-fluoroethyl, 1-iodoethyl, 2-iodoethyl, 1-chloropropyl, 2-chloropropyl, 3-chloropropyl, 1-bromopropyl, 2-bromopropyl, 3-bromopropyl, 1-fluoropropyl, 2-fluoropropyl, 3-fluoropropyl, 1-iodopropyl, 2-iodopropyl, 3-iodopropyl, 2-aminopropyl, 1-aminoethyl, N-benzoyl-2-aminoethyl, N-acetyl-2-aminoethyl, N-benzoyl-1-aminoethyl, N-acetyl-1-aminoethyl and the like.

Examples of the above substituted alkenyl groups include styrolyl, 3-chloropropen-1-yl, 3-chlorobuten-1-yl, 3-methoxypropen-2-yl, 3-phenylbuten-2-yl, 1-cyanobuten-3-yl and the like. The type of stereoisomerism is not essential, and all stereoisomers can be used for a respective substituted alkenyl.

The term "alkinyl," as used here, preferably refers to a radical of the formula R—C≡C—, in particular a "$C_2$-$C_6$alkinyl." Examples of $C_2$-$C_6$ alkinyls include: ethinyl, propinyl, 2-butinyl, 2-pentinyl, 3-pentinyl, 2-hexinyl, 3-hexinyl, 4-hexinyl, vinyl and dienes and trienes of linear and branched alkyl chains.

The term "aryl," as used herein, preferably refers to aromatic hydrocarbons, for example phenyl, benzyl, naphthyl, or anthryl. Substituted aryl groups are aryl groups which, as defined above, are substituted with one or a plurality of substituents.

The term "cycloalkyl" preferably comprises the cyclopropyl, cyclobutyl, cyclopentyl, cyclohexyl, cycloheptyl and adamantane groups.

The term "cycloalkenyl" preferably comprises substituted or unsubstituted cyclic groups such as cyclopentenyl or cyclohexenyl. The term "cycloalkenyl" also covers cyclic groups with conjugated double bonds such as e.g. cyclohexadiene.

The term "alkenyl" comprises, within the meaning of the present application, groups with one or a plurality of double bonds, wherein the double bonds can also be in conjugated form, such as e.g. butadienes.

The term "heteroaryl" refers to a heterocyclic aromatic derivative that has a five-membered or six-membered ring system with 1-4 heteroatoms, such as e.g. oxygen, sulfur and/or nitrogen, in particular nitrogen, either alone or together with sulfur or oxygen ring atoms. Examples of heteroaryls include pyridinyl-, pyrimidinyl, pyrazinyl, pyridazinyl, pyrrolo, furano, oxazolo, isooxazolo, phthalimido, thioazolo and the like. The term "substituted heteroaryl" refers to the above-described heteroaryl, which for example is substituted with one or a plurality and preferably one or two substituents that are as described above.

The term "$C_7$-$C_{18}$ alkylphenyl" refers to a $C_1$-$C_{12}$ alkyl group that is substituted with a phenyl radical at any desired position in the alkyl chain. The definition includes the groups of the formula -phenyl-alkyl, -alkyl-phenyl-, and alkyl-phenyl-alkyl-. Examples of "$C_7$-$C_{18}$ alkylphenyl" include benzyl, 2-phenylethyl, 3-phenyl(n-propyl), 4-phenylhexyl, 3-phenyl(n-amyl), 3-phenyl(s-butyl) and the like. Preferred $C_7$-$C_{18}$ alkylphenyl groups are all of the preferred alkyl groups described herein, in combination with a phenyl group. The term "substituted $C_7$-$C_{18}$ alkylphenyl" refers to a $C_7$-$C_{18}$ alkylphenyl group, as described above, in which the alkyl radical and/or the phenyl radical is substituted with one of the groups defined above as substituents.

The term "$C_3$-$C_7$ cycloalkyl" comprises the groups cyclopropyl, cyclobutyl, cyclopentyl, cyclohexyl and cycloheptyl.

The term "$C_5$-$C_7$ cycloalkenyl" refers to a 1, 2, or 3 cyclopentenyl ring, a 1, 2, 3, or 4 cyclohexenyl ring or a 1, 2, 3, 4, or 5 cycloheptenyl ring. The term "substituted $C_5$-$C_7$ cycloalkenyl" refers to a $C_5$-$C_7$ cycloalkenyl ring, as described above, that is substituted with a $C_1$-$C_{12}$ alkyl radical, halogen, hydroxy, protected hydroxy, $C_1$-$C_{12}$ alkoxy, trifluoromethyl, carboxy, protected carboxy, oxo, protected oxo, monosubstituted amino, protected monosubstituted amino, disubstituted amino, phenyl, substituted phenyl, amino or protected amino.

The term "alkylene" refers to a group —(CRaRb)x-, wherein Ra and Rb can be H or one of the above-mentioned substituents and x≥1, wherein x=1, 2, or 3 is preferred.

The term "heteroalkylene" refers to an alkylene group in which at least one C atom is replaced by a heteroatom such as N or O.

As mentioned many times above, the present catalyst is used for the hydroformylation of olefins. The olefins used in hydroformylation include styrene or $C_3$-$C_{15}$ olefins, preferably $C_7$-$C_{12}$ olefins, such as 1-octene or 1-dodecene. Functionalized olefins such as allyl alcohols, alkenyl ethers, alkenyl esters, or conjugated olefins are also of further industrial importance.

The hydroformylation of olefins in the presence of the catalyst according to the invention (formed in situ) is preferably carried out at a pressure of between 10 and 100 bar, preferably between 20 and 70 bar, particularly preferably between 30 and 50 bar, and a temperature of between 50 and 150° C., preferably between 50 and 100° C.

In a variant embodiment, the hydroformylation reaction comprises the following steps:
  preparation of a reaction mixture of at least one NHSi ligand and at least one metal precursor in a suitable solvent and addition of at least one substrate for the hydroformylation in a suitable reactor, preferably under an inert gas atmosphere;
  addition of synthesis gas (of carbon monoxide and hydrogen) to the reaction mixture in the reactor; and
  carrying out the hydroformylation reaction at a temperature of between 50 and 100° C. and a pressure of between 10 and 50 bar, preferably 30 and 50 bar.

As solvents, aromatic solvents such as toluene, benzol or o, m, p-xylene are used.

In an additional further variant, the hydroformylation reaction comprises the following steps:
  Preparation of the reaction mixture: The reaction mixture was prepared using standard Schlenk techniques. The metal precursor and the corresponding ligand were weighed in. For this purpose, freshly distilled substrate and solvents were added. In a variant, toluene was used as a solvent and styrene as a substrate.
  Inertization of the reactor: The hydroformylation reactions were carried out in a 100 ml stainless steel autoclave. The reactor was heated for one hour at 110° C. and then evacuated 3× and flushed with nitrogen.
  Filling of the reactor with the reaction mixture: The reaction mixture was injected with a syringe under a nitrogen counterflow at reaction temperature.
  Setting of process conditions: After the reactor was filled, it was closed. The reactor was filled with synthesis gas, wherein the pressure was 30 bar. The use of synthesis gas was controlled by means of a mass flow controller so that isobaric conditions prevailed during the reaction. The temperature for all reactions was between 50° C. and 100° C.
  Sampling and analysis: Samples for determining conversion rate and catalytic activity were taken at regular intervals, diluted with acetone, and examined by gas chromatography.

In a variant of the present hydroformylation method, the catalyst is formed in situ in the reaction mixture from the ligand and a precursor complex comprising the metal, wherein preferably 3 eq. of the ligand and 0.01 mmol of the metal are used.

BRIEF DESCRIPTION OF THE DRAWING

The invention is explained in the following by means of several examples with reference to the figures.

FIG. 1 shows a schematic illustration of the catalysis cycle of rhodium-catalyzed hydroformylation.

DETAILED DESCRIPTION

Example 1: Production of a First NHSi Ligand (1)

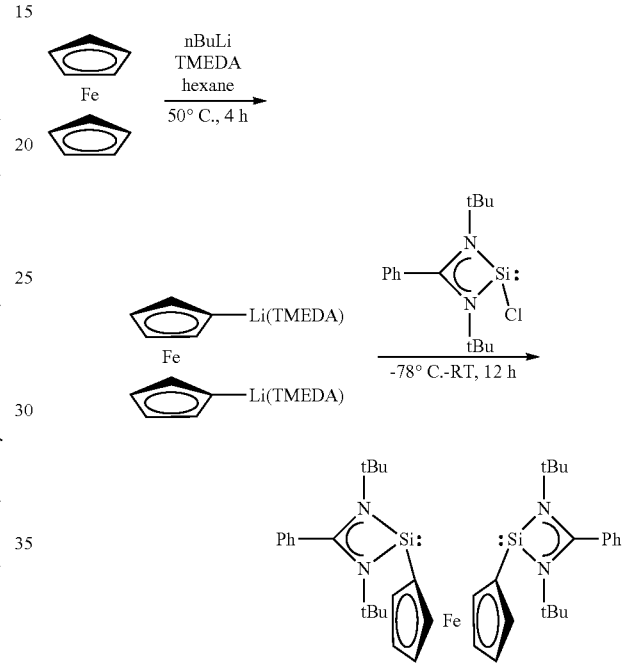

All of the experiments were carried out using standard Schlenk techniques with dry nitrogen as an inert gas. 1.6 M n-butyllithium (4.23 mL, 6.77 mmol) was added at 0° C. to a solution of hexane (10 mL) with ferrocene (600 mg, 3.23 mmol) and TMEDA (937 mg, 8.06 mmol). The reaction solution was stirred for 4 hours at 50° C. The reaction solution was then cooled to −78° C. A solution of the chlorosilylene (1.9 g, 6.45 mmol) in toluene (30 mL) was added dropwise to this for 5 min. The mixture was stirred overnight at room temperature, after which all of the volatile components were removed under a vacuum, and the residue was extracted with pentane. The dark-red crystals of (1) were stored in pentane at 0° C.

$^1$H-NMR (400.13 MHz, $C_6D_6$, 298K, ppm): δ=1.16 (s, 36H, NC(CH$_3$)$_3$), 4.51 (t, $^3$J (H,H)=1.5 Hz, 4H, FeCH), 4.72 (t, $^3$J (H,H)=1.5 Hz, 4H, FeCH), 6.92-7.07 (m, 10H, arom. H); $^{13}$C{$^1$H} NMR (100.61 MHz, $C_6D_6$, 298K, ppm) δ=31.8 (NC(CH$_3$)$_3$), 53.0 (NC(CH$_3$)$_3$), 70.9 (FeCH), 72.7 (FeCH), 84.6 (SiC), 128.9, 129.4, 130.5, 134.9 (arom. C), 160.4 (NCN); $^{29}$Si {$^1$H} NMR (79.49 MHz, $C_6D_6$, 298K, ppm) δ=43.3;

Characterization of the corresponding rhodium complex HRh (CO) (PPh$_3$):

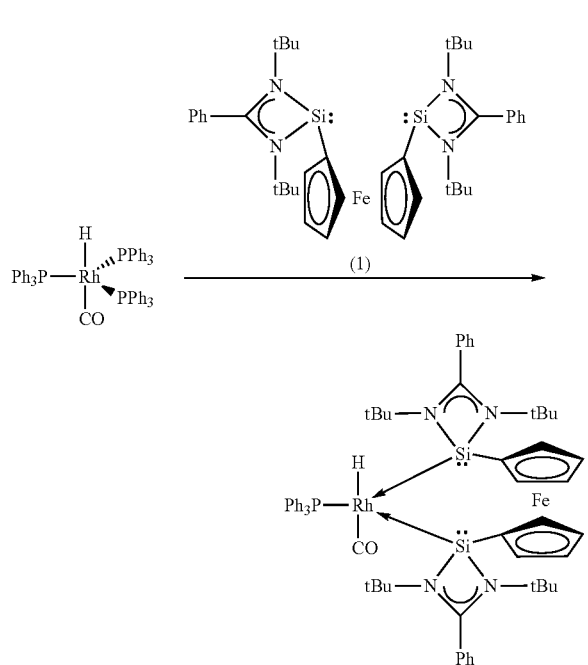

The rhodium precursor tris(triphenylphosphine)hydrido-carbonyl-rhodium (I) HRh(CO) (PPh$_3$)$_3$ and the NHSi ligand (1) were dissolved in an equimolar ratio in 0.5 ml of C$_6$D$_6$. An orange coloration was immediately observed. NMR results confirm the formation of the rhodium complex HRh(CO) (PPh$_3$) (1).

$^2$H-NMR (200 MHz, THF-d$_8$, 298 K, ppm): δ=−9.43 (ps t: 1H, $^1$J (H,Rh) and $^2$J (H,P)=11.4 Hz) (P coupling visible), 0.87 (s, 18H, 2×H-$^t$Bu-N), 1.29 (s, 18H, 2×H-$^t$Bu-N), 4.15 (m, 8H, 4×H-ferrocenes), 7.03-7.70 (m, 55H, H-PPh$_3$+m, 10H, H-Ph). $^{31}$P-NMR (81 MHz, THF, 298 K, ppm): δ=−5.4 (s, P-PPh$_3$) (free ligand), 44.7 (d, $^1$J (P,Rh)=98.7 Hz).

On addition of an excess of the NHSi ligand, the rhodium complex HRh(CO) (PPh$_3$) was also formed, wherein excess ligand was not reacted.

Example 2: Production of a Second NHSi Ligand (2)

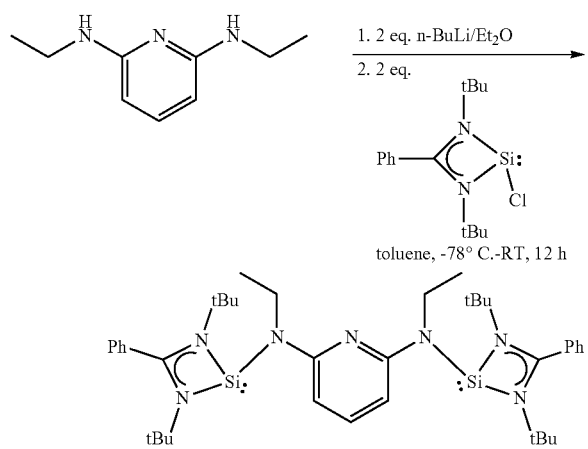

$^1$H-NMR (400.13 MHz, C$_6$D$_6$, 298 K, ppm): symmetric conformer: δ=1.16 (s, 36H, NC(CH$_3$)$_3$), 1.63 (t, $^3$J (H,H)=6.9 Hz, 6H, NCH$_2$—CH$_3$), 3.77 (q, $^3$J (H,H)=6.9 Hz, 4H, NCH$_2$—CH$_3$), 6.87-7.09 (m, 10H, arom. C—H), 7.34-7.50 (m, 3H, arom. C—H py.). Asymmetric conformer: δ=1.14 (s, 36H, NC(CH$_3$)$_3$), 1.55 and 1.68 (t, $^3$J (H,H)=6.9 Hz, 6H, NCH$_2$—CH$_3$), 3.71 and 4.62 (q, $^3$J (H,H)=6.9 Hz, 4H, NCH$_2$—CH$_3$), $^{13}$C{$^1$H}-NMR (100.61 MHz, C$_6$D$_6$, 298 K, ppm): symmetric conformer: δ=16.9 (NCH$_2$—CH$_3$), 31.6 (NC(CH$_3$)$_3$) 31.9 (NCH$_2$—CH$_3$), 52.9 (NC(CH$_3$)$_3$), 101.8 (3.5-C$_{arom.}$ py), 127.6 (C$_{arom}$), 128.5 (C$_{arom}$), 129.3 (C$_{arom}$), 129.3 (C$_{arom}$), 129.4 (C$_{arom}$), 130.0 (C$_{arom}$), 130.5 (C$_{arom}$), 130.5 (C$_{arom}$), 134.7 (C$_{arom}$ quaternary Ph), 136.9 (4-C$_{arom}$ py), 161.2 (2,6-C$_{arom}$ py), 161.4 (NCN). Asymmetric conformer: δ=18.0 and 16.0 (NCH$_2$—CH$_3$), 31.4 and 31.5 (NC(CH$_3$)$_3$), 36.8 and 43.9 (NCH$_2$—CH$_3$), 53.3 (NC(CH$_3$)$_3$), 103.0 and 103.9 (3,5-C$_{arom.}$ py), 134.0 and 134.5 (C$_{arom}$ quaternary Ph), 136.4 (4-C$_{arom}$ py). $^{29}$Si{$^1$H}-NMR (79.49 MHz, C$_6$D$_6$, 298 K, ppm): symmetric conformer: δ=−14.9. Asymmetric conformer: δ=−13.8 and −17.1.

Example 3: Hydroformylation

Preparation of Reaction Mixture:

The rhodium precursor HRh(CO) (PPh$_3$)$_3$ (0.01 mmol, 9.188 mg, 1 eq.) and the NHSi ligand (1) (3 eq.) were first placed in a 100 ml Schlenk flask and dissolved in freshly distilled toluene (0.434 mol, 40.0 g). Freshly distilled styrene (0.038 mol, 4.0 g, 3,800 eq.) was then added.

Experimental Procedure for Hydroformylation of Styrene:

Hydroformylation was carried out in a 100 ml stainless steel autoclave. Before adding the reaction mixture, the reactor was heated at 110° C. for one hour and then evacuated 3× in each case and flushed with nitrogen. After cooling to reaction temperature, the reaction mixture was injected into the reactor with a syringe under a nitrogen counterflow. After this, a reaction pressure of 30 bar synthesis gas (1:1 hydrogen and carbon monoxide) was applied in the reactor with a stirring rate of 200 rpm, and after the reaction pressure was reached, the stirring rate was increased to 1200 rpm. In order to achieve isobaric reaction conditions, converted synthesis gas was added by means of a mass flow controller. Samples were diluted with acetone and analyzed by gas chromatography.

FIG. 1 illustrates a catalytic cycle of a rhodium catalyst with a bidentate ligand, beginning with the trigonal-bipyramidal hydride species 6, which is produced in situ according to the above reaction equation. The formation of active complex 7 is initiated by the loss of a triphenylphosphine ligand. π coordination of the alkene on the unsaturated rhodium complex 7 leads to the formation of complex 8, after which migration of the hydride leads to the corresponding rhodium-alkyl complex 9. After coordination of an additional CO molecule with the formation of complex 10, CO is introduced into the rhodium-alkyl bond, forming the rhodium-acyl complex 11. By addition of hydrogen, which leads to the formation of complex 12, the aldehyde 12 is separated, and the active rhodium-hydride complex 7 is regenerated.

In order to assess catalytic activity with the bidentate ligand according to the invention (indicated by (1) in the table), hydroformylation of styrene was investigated by comparison of XantPhos, a commonly-used bidentate phosphine ligand. In this case, "turnover frequency" (TOF), which describes the number of catalytic cycles of the catalyst per unit time, was used as a characteristic parameter. The results for various temperatures are shown in Table 1.

TABLE 1

TOF values for the hydroformylation of styrene with bidentate ligands at various temperatures. Reaction conditions: 40 g toluene, 4 g styrene, $n_{Rh}$ 0.01 mmol, $n_{ligand}$ = 3 eq, p = 30 bar, rpm = 1200. TOF determined after 60 min at 50° C., after 30 min at 80° C., and after 10 min at 100° C.

| Ligand | Temperature T [° C.] | TOF$^a$ [1/h] |
|---|---|---|
| (1) | 50 | 83 |
| XantPhos | 50 | 32 |
| (1) | 80 | 2621 |
| XantPhos | 80 | 646 |
| (1) | 100 | 9075 |
| XantPhos | 100 | 3007 |

As can be seen from Table 1, the TOF at all of the temperatures in use of the bidentate NHSi ligand according to the invention (1) was tripled compared to XantPhos, which indicates a clear increase in activity. The catalyst also remains stable at high temperatures.

The invention claimed is:

1. A catalyst for the hydroformylation of at least one olefin comprising,
a ligand of general formula (I)

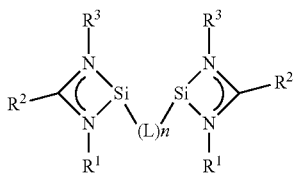

R1, R2 and R3 are selected from the group comprising substituted and unsubstituted alkyl, substituted and unsubstituted aryl, substituted and unsubstituted alkenyl, substituted and unsubstituted alkinyl, substituted and unsubstituted cycloalkyl, substituted and unsubstituted heterocycles,
wherein R1, R2 and R3 can each be the same or different,
L is selected from a group comprising a sandwich complex, an oxygen group, substituted and unsubstituted alkylene or heteroalkylene, substituted aryl or heteroaryl, wherein aryl and heteroaryl are each substituted with groups comprising at least two heteroatoms and are coupled to the Si via the at least two heteroatoms of the substituents,
n=1-10;
wherein the ligand is coupled to the metal M from group VIIIb of the periodic table of elements via the Si group, wherein M is Rh;
wherein ligand and metal form a complex of general formula (II)

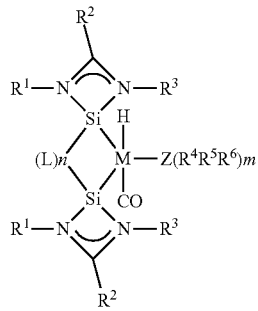

wherein
Z is a non-metallic element of group Va of the periodic table of elements or a CO ligand,
R4, R5, and R6 are selected from the group comprising substituted and unsubstituted alkyl, substituted and unsubstituted aryl, substituted and unsubstituted alkenyl, substituted and unsubstituted alkinyl, substituted and unsubstituted cycloalkyl, substituted and unsubstituted heterocycles,
wherein R4, R5, and R6 can each be the same or different, and
m=0-3.

2. The catalyst as claimed in claim 1, wherein Z is phosphorus or nitrogen.

3. The catalyst as claimed in claim 1, wherein R4, R5, and R6 are selected from the group comprising substituted and unsubstituted C1-C12 alkyl, substituted and unsubstituted phenyl, substituted and unsubstituted C5-C6 heteroaryl, substituted and unsubstituted naphthyl, substituted and unsubstituted C3-C7 cycloalkyl, substituted and unsubstituted C7-C18 alkylphenyl, substituted and unsubstituted C5-C7 cycloalkenyl, and substituted and unsubstituted C2-C7 heteroalkylene.

4. The catalyst as claimed in claim 1, wherein R4, R5, R6 are selected from the group comprising substituted and unsubstituted phenyl.

5. The catalyst as claimed in claim 1, wherein m=3.

6. A method for the hydroformylation of olefins in the presence of a catalyst comprising
a ligand of general formula (I)

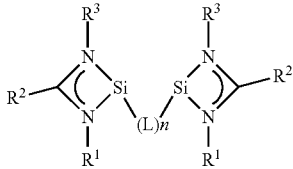

wherein
R1, R2 and R3 are selected from the group comprising substituted and unsubstituted alkyl, substituted and unsubstituted aryl, substituted and unsubstituted alkenyl, substituted and unsubstituted alkinyl, substituted and unsubstituted cycloalkyl, substituted and unsubstituted heterocycles,
wherein R1, R2 and R3 can each be the same or different,
L is selected from a group comprising a sandwich complex, an oxygen group, substituted and unsubstituted alkylene or heteroalkylene, substituted aryl or heteroaryl, wherein aryl and heteroaryl are each substituted with groups comprising at least two heteroatoms and are coupled to the Si via the at least two heteroatoms of the substituents, n=1-10, preferably 1-5, particularly preferably 1, 2, or 3; and wherein the ligand is coupled to the metal M from group VIIIb of the periodic table of elements via the Si group, comprising the following steps:

preparation of a reaction mixture of at least one NiHs ligand and at least one metal precursor in a suitable solvent and addition of at least one substrate for the hydroformylation in a suitable reactor, under an inert gas atmosphere;

addition of synthesis gas of carbon monoxide and hydrogen to the reaction mixture in the reactor; and carrying out the hydroformylation reaction at a temperature of between 50 and 100° C. and a pressure of between 30 and 50 bar.

7. The method as claimed in claim 6, wherein the catalyst is formed from the ligand and a precursor complex comprising the metal in situ in the reaction mixture.

8. The method as claimed in claim 6, wherein M is Co or Rh.

9. The method for hydroformylation of olefins as claimed in claim 6 the hydroformylation of styrene and C3-C15 olefins.

10. A method as claimed in claim 6 for the hydroformylation of styrene and 1-octene or 1-dodecene.

* * * * *